United States Patent [19]

Krumeich et al.

[11] Patent Number: 4,884,570

[45] Date of Patent: Dec. 5, 1989

[54] DEVICE FOR RETAINING A DISC OBTAINED FROM A HUMAN CORNEA

[75] Inventors: Jorg H. Krumeich, Bochum; Norbert Quast, Essen-Kray, both of Fed. Rep. of Germany

[73] Assignee: EyeTech AG, Liechtenstein, Liechtenstein

[21] Appl. No.: 712,249

[22] Filed: Mar. 15, 1985

[30] Foreign Application Priority Data

Mar. 16, 1984 [DE] Fed. Rep. of Germany ........ 3409798

[51] Int. Cl.4 .............................................. A61B 17/32
[52] U.S. Cl. .................................. 128/305; 128/303 R
[58] Field of Search ............................ 128/303 R, 305

[56] References Cited

U.S. PATENT DOCUMENTS

| | | | |
|---|---|---|---|
| 3,058,471 | 10/1962 | Shape | 128/305 |
| 3,074,407 | 1/1963 | Moon et al. | 128/303 R |
| 3,129,971 | 4/1964 | Kobler | 128/303 R |
| 3,139,298 | 6/1964 | Grabiel | 128/303 R |
| 4,077,411 | 3/1978 | Ward | 128/305 |
| 4,236,519 | 12/1980 | La Russa et al. | 128/305 |
| 4,526,171 | 7/1985 | Schachar | 128/305 |
| 4,660,556 | 4/1987 | Swinger et al. | 128/305 |

Primary Examiner—Michael H. Thaler
Attorney, Agent, or Firm—Clifford A. Poff

[57] ABSTRACT

Apparatus to retain a disc obtained from a human cornea during a cutting operation to alter the surface of the disc. The apparatus includes a plurality of plunger-like moldings, any one of which can support the corneal disc. The molding is interchangeably supported in a recess provided in a support member. The support surface of the molding is concave or convex with a predetermined curvature and gaspervious openings communicate with an evacuation chamber so that a corneal disc can be sucked against the corneal support surface by a negative pressure. A pressure ring engages the edge of the corneal disc for clamping it between the pressure ring and molding. A guideway for a transversely-movable cutting device ring and molding. The molding can be formed with a number of bores or constructed of porous material. The apparatus is used by selecting a particular molding with a corneal disc-receiving surface that is either convex when minus values are required or concave when plus values are required.

22 Claims, 2 Drawing Sheets

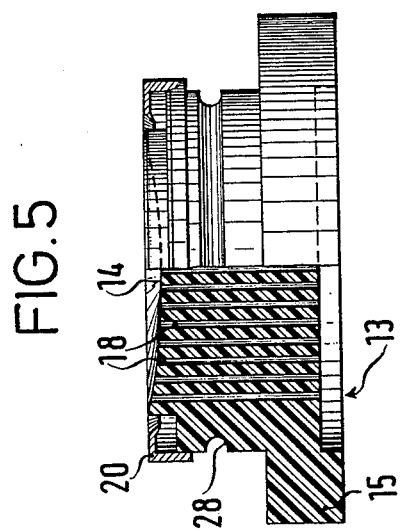
FIG.5
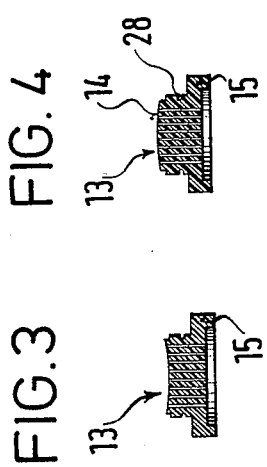
FIG.4
FIG.3
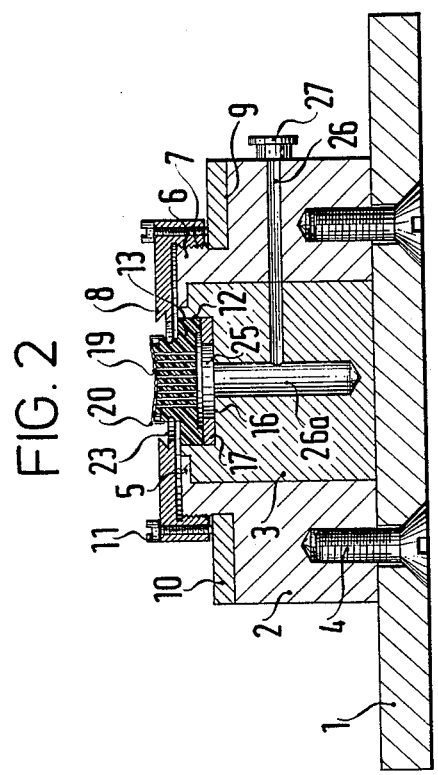
FIG.2
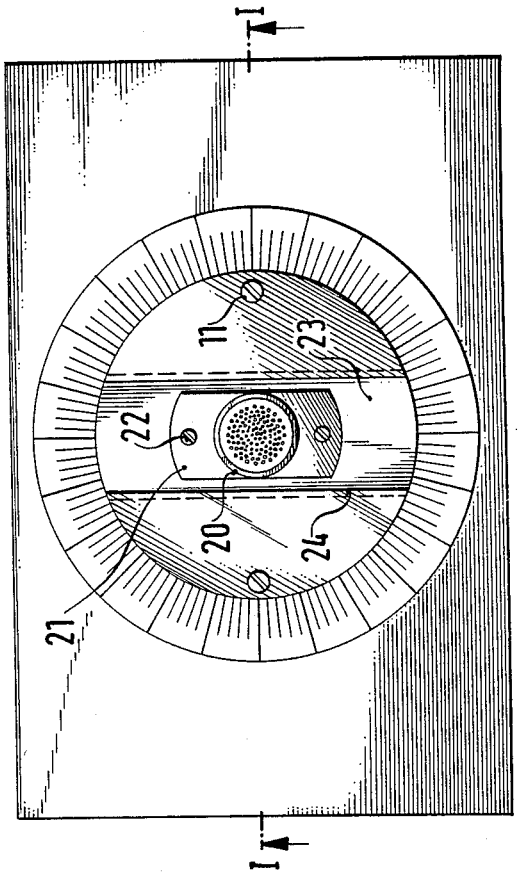
FIG.1

DEVICE FOR RETAINING A DISC OBTAINED FROM A HUMAN CORNEA

BACKGROUND OF THE INVENTION

This invention relates to a device, more particularly an apparatus for retaining a disc obtained from a human cornea during cutting thereof to alter the surface of the corneal disc.

It is known in the field of ophthalmology that faulty vision can be corrected by altering the refractive power of an eye through transplanting a plane-parallel disc which has been obtained from a human cornea and provided with a surface that is shaped to a predetermined radius. An appliance for obtaining plane-parallel cornea discs is disclosed in West German Patent Publication No. 3,147,662. In conventional technology for altering the surface of a corneal disc, a plastic disc is turned on a lathe to form a recess having a radius corresponding to the outside radius of a disc obtained from a human cornea. Thereafter, the corneal disc is quickly frozen in the recess of the plastic disc and two surface curvatures are obtained by computer calculations of which one curvature is the inner optical zone and the other curvature is for the edge.

This process, known as keratomileusis, has a major disadvantage because of the requirement for complicated technological use of the lathe, the refrigeration technology, chemical pretreatment of the disc and chemical after treatment of the disc. The process involves about 70 steps and for optimum results, some of the steps must be carried out within a sharply defined period of time.

SUMMARY OF THE INVENTION

It is an object of the present invention to considerably simplify the processing of a corneal disc in order to obtain a curved corneal disc surface having calculated radii of curvature and to obviate the disadvantages of the known process as hereinbefore set forth.

According to the present invention, there is provided an apparatus for retaining a disc obtained from a human cornea during treatment thereof in which the apparatus includes the combination of a rigid support member, a gas-pervious molding removably carried by the rigid support member for supporting a disc of a human cornea, the gas-pervious molding having a circular disc receiving surface with a predetermined curvature, means forming an evacuation chamber for communication with the gas-pervious molding, a pressure ring releasably engaging an edge of the gas-pervious molding for clamping an edge of a disc of a human cornea between the pressure ring and the gas-pervious molding, a guideway means for supporting a cutter to move transversely of the disc-receiving surface and means for adjusting the height of the guideway means relative to the gas-pervious molding.

The human corneal disc for processing by use of the apparatus of the present invention is obtained the same way as is conventional, for example, by means of micrkeratom as described in West German Patent Publication No. 3,147,622. A corneal disc prepared in this way is placed on the gas-pervious molding so that the outside surface of the disc is in contact with the gas-pervious molding and held in position by a suction applied to the disc by way of a vacuum and further by the pressure ring which is releasable.

The gas-pervious molding is selected in accordance with a previously measured radius of the cornea and the required refraction. The molding is then placed in the rigid support member. The support surface of the molding for the corneal disc has, according to the required refractive power, either a fairly substantial convexity if minus values are required or a fairly substantial concavity if plus values are required. The corneal disc is thus shaped on the selected molding and then can be given, by means of a cutting knife or the like, a surface cut along a straight path instead, according to the conventional processes, along the curves which had to be turned into the corneal disc on a lathe.

By means of the apparatus according to the present invention, the corneal disc for treatment is, so to speak, brought into its negative form by pushing the disc over a rod-like plunger. Only in this way can the inside of the corneal tissue be processed with a straight cut. Conveniently, appropriate moldings are stored in required numbers for different refractions. A particular molding can then be selected and placed in the retaining device to suit an individual requirement.

For transmission of the negative pressure to the top of the molding, the molding can be made of porous material or formed with a number of plurality of through-bores distributed about the support surface for the corneal disc for transmission of the negative pressure to the top of the molding.

Advantageously, a screw-threaded cover is rotatable on screw threads formed on a rigid member of the apparatus. The cover extends concentrically around the molding for vertical adjustment of a guideway for the cutting device. Conveniently, the pressure ring is formed with lugs on diametrically-opposite sides and each lug is provided with a bore adapted to receive a fastening screw for securing the pressure ring. The molding is provided with a retaining flange on its bottom end for positively engaging with a retaining flange on its bottom end for positively engaging in a bore in a lower support member of the apparatus for securing the the molding in its operative position. The cutting knife, which can be a microkeratom as described in West German Patent Publication No. 3 147 662, is moved on the guideway and conveniently guided by means of laterally, spaced-apart dovetailed guides that form rails. A straight cut performed by the cutting knife can be made equally satisfactorily with a rapidly rotating wire or with a laser beam.

The main advantages of the present invention over the conventional method include accurate processing of a corneal disc without the need for a high precision lathe; the cornea is not subject to chemical action by a cryopreservation solution and by a thawing solution; elimination of the step of freezing the cornea; lower equipment costs than for conventional facilities; and a considerable saving of time to perform the cutting operation.

These features and advantages of the present invention as well as others will be more fully understood when the following description is read in light of the accompanying drawings, in which:

FIG. 1 is a plan view of a retaining apparatus according to an embodiment of the present invention;

FIG. 2 is a sectional view taken along line I—I of FIG. 1;

FIG. 3 is a sectional view through a gas-previous molding having a concave corneal support surface;

FIG. 4 is a cross-sectional view through a gas-pervious molding having a convex corneal support surface;

FIG. 5 is an enlarged view, partly in section, through a gas-pervious molding and cornea-retaining ring.

Figure 6:
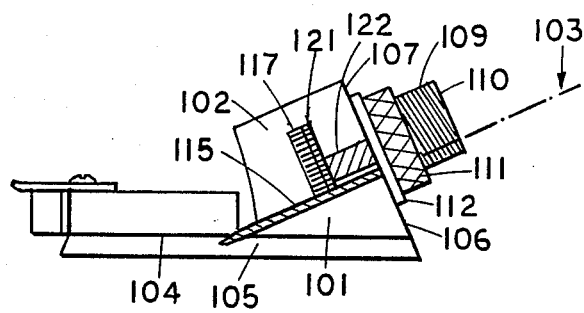
FIG. 6 is an elevational view of a corneal microtome partly in section for cutting of a corneal disc according to the present invention.
Figure 7:
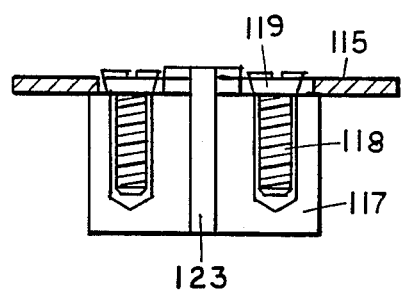
FIG. 7 is an elevational view of the knife holder in longitudinal section to an enlarged scale.
Figure 8:
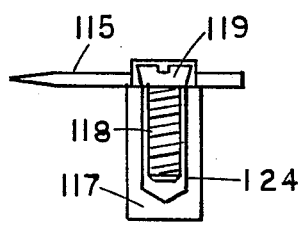
FIG. 8 is a cross-sectional view of the knife holder in the axial plane of a fasting screw.
Figure 9:
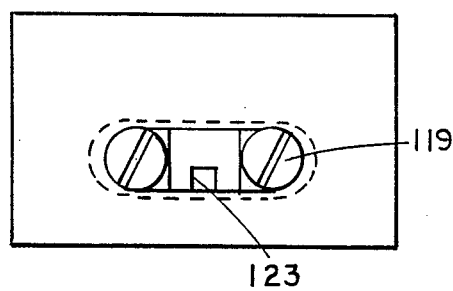
FIG. 9 is a view of the underside of the knife holder with the fastening screws.
Figure 10:
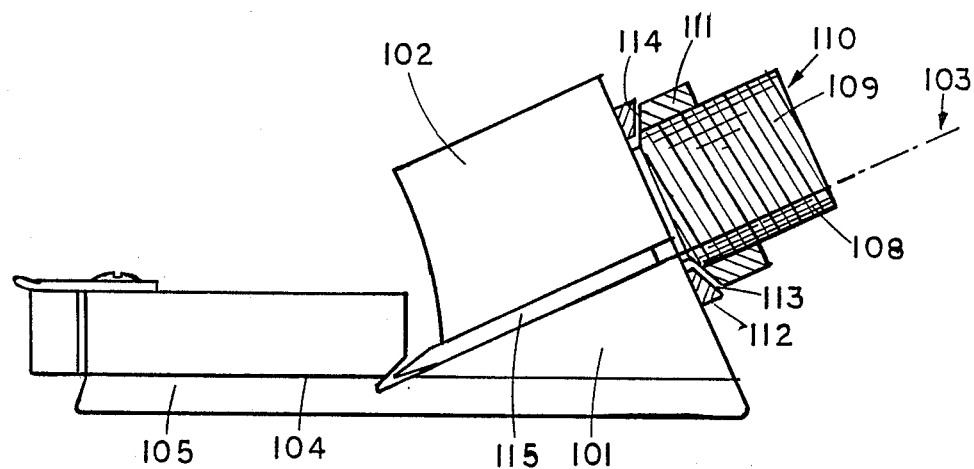
FIG. 10 is an enlarged elevational view of the corneal microtome with a longitudinal section in the region of the split threaded cock.

The apparatus of the present invention includes a rectangularly-shaped base plate 1 on which there is supported an outer retaining ring 2 and an inner cylindrical carrier 3 that is secured to the base plate. Ring 2 is secured to the base plate 1 by screw fasteners 4. The top end of ring 2 is formed with a flange ring 5 which projects inwardly in relation to the bore, wherein carrier 3 is received and engages in a correspondingly-shaped peripheral recess in the carrier 3. The external top part of ring 2 is provided with a reduced diameter to form a neck part 6 and provided on the outer surface thereof are fine screw threads 7 adapted to threadedly engage with similar screw threads formed on a ring cover 8 for vertical adjustment thereof. A radial shoulder 9 formed on ring 2 bears on a ring 10. The shoulder 9 is part of the transition to the neck part 6. The ring 10 is provided with a division scale on its top surface for angular adjustment of the cover 8. Threaded pins 11 are retained in tapped bores with parallel axes for establishing the location of the cover 8. The free ends of the screws 11 can be pressed against ring 10 to retain the cover at any required relative angular position.

The carrier 3 is formed with a central circular recess 12 at its top end wherein a plunger-like, gas-pervious molding 13 can be engaged. A circular surface 14 of the molding 13 is shaped either concave or convex. A retaining flange 15 is formed on the bottom end of the molding 13 for positive engagement in recess 12. In the embodiment of the apparatus shown, a compensating ring 17 is introduced between the flange 15 and a base 16 of the recess 12; however, if the depth of the recess 12 and the height of the flange 15 are appropriately dimensioned, the ring 17 can be omitted. As illustrated in FIGS. 1-5, a number of bores 18 having axes which are parallel to one another extend through the molding 13. A cylindrical outer wall of the molding 13 is formed with a peripheral groove 28 to ensure that a molding 13 which is relatively small can be firmly gripped when introduced into and removed from the recess 12 in carrier 3. Preferably, the molding is made of an appropriately hard plastic material. The molding 13 extends in its operative position with an adequate clearance through an inner aperture in cover 8. The surface 14 of the molding is higher than the surface of the cover 8. In FIG. 2, a disc 19 which has been taken from a human cornea is supported on the surface 14 of the molding. An edge of disc 19 is bent around the edge of the disc-receiving surface 14 of the molding.

A pressure ring 20 is provided to press a bent edge of a corneal disc on the molding 13 and by way of its inside edge, presses the bent edge of the corneal disc onto the wall of the molding 13. Lugs 21, each formed with at least one through-bore, are formed on diametrically-opposite sides of the pressure ring 20. The lugs 21 and, therefore, the pressure ring 20 can be clamped on the cover 8 by means of screws 22.

A planar guideway 23 is cut in a diametrical direction in the surface of cover 8. The guideway is bound along parallel sides by dovetailed guides 24. A cutting device is slideably guided along the guideway during the cutting step. The cutting device for this purpose is of the type shown in FIGS. 6–10 and disclosed in West German Patent Publication No. 3,147,662.

As shown in FIG. 6, the head of the corneal microtome is formed of an underpart 101 and an upper part 102 which is detachably connected to the underpart 101 along a dividing plane 103. The dividing plane is inclined to the planar underside 104 of the lower part 101. On both longitudinal edges, the underside 104 is bounded by projecting ridges 105, which are dove-tail shaped in cross-section and serve for join the head of the microtome for reciprocating movement along the parallel dovetail guides 24 and the planar guideway 23.

Each of the underpart 101 and upper part 102 of the head contain on their co-planar back-sides 106 and 107 a threaded cock 110 integrally formed with the upper part 101 or lower part 102, that together form the threaded cock, which is split in the dividing plane 103. The threaded cock 110 is provided with a central bore, in which a drive (not shown) for the knife is fed, by which it is retracted or advanced.

For the reciprocal tensioning of the lower and upper parts 101 and 102 there is a threaded ring 111. After the assembly of the two parts 101 and 102, the ring 111 is threaded onto the threaded cock 110. Previously there was pushed onto the threaded cock 110 an intermediate ring 112, which lies against the back sides 106 and 107 of the parts 101 and 102. Ring 112 includes a conical surface 113 sloping towards the cock axis. A threaded ring 111 is provided on its inner face side with a corresponding conical surface 114.

Upon drawing tight of the threaded ring 111, there develops simultaneously with the tensioning a definite reciprocal fixing of the two parts of the corneal microtome, which excludes unwanted relative displacements. Tipping or canting of the two parts is prevented by the engaging conical surfaces, as they usually can be seen to have pressure surfaces that are perpendicular to the cock axis. Instead of an integral intermediate ring, there can also be used an intermediate ring that is split in the dividing plane 103, whereby the ring parts either are bound fast with the corresponding parts of the head or are held by surrounding grooves, in which they are inserted.

Between the two parts 101 and 102 of the head, there is located in a guide slit running parallel to the dividing plane a flat knife 115 with an approximately rectangular outline. The cutting edge of the knife 15 protrudes insignificantly from the underside 104 of the lower part 101. The knife 115 is detachably connected to a knife-holder 117, which principally has the form of a rectangular prism. The holder consists of artificial material (plastic) with low frictional resistance, as, for example, polytetrafluoroethylene. The knife 115 is fastened detachably with the aid of two screws 118 to the knife holder 117. Each screw 118 is screwed into an interiorly threaded bore 124. The screws 118 have a screw head in frustroconical form which extends only partway into the fastening bores 120 located in the knife 115, so that with the drawing tight of the screws 118, the knife 115 is at the same time fixed against side displacements by the conical form of the screwhead 119.

The knife holder 117 is slidingly guided in a recess 121 in the upper part 102 of the head so that the holder may execute forward and backward movements in a plane running horizontal to the cock axis. In the recess 121 there begins a central bore 123 extending through the cock 110 for the reception of the rotating drive which brings about the oscillating movement of the knife 115. This drive contains on its free end an eccentric pin, which engages in a guide slit 123 of the knifeholder 117. A revolution of the drive thus corresponds to a complete oscillating movement of the knife holder 117 and thus of the knife 115.

Returning now to FIG. 2, a chamber 25 is disposed below the gas-pervious molding 13 and communicates by way of a duct 26 with an external connector 27. A negative pressure can be produced in chamber 25 by means of an exhauster to cause disc 19 to be pressed flatly against the surface 14 and thereby obviate the risk of movement of the disc 19 during a cutting operation. Before a disc 19 is placed on the molding 13, the cover 8 is first turned to bring the guideway to a required height in relation to surface 14 of a particular molding 13 which is selected. Thereafter, the cover 8 is secured by tightening screws 11. The disc 19 can now be placed on surface 14 and thereafter pressure ring 20 is positioned. A predetermined negative pressure is produced in chamber 25 before the cut is made.

Conveniently, the selection of a particular molding 13 required for a number of different moldings and the requisite vertical adjustment of cover 8 are based on precalculated and tabulated data.

Although the invention has been shown in connection with a certain specific embodiment, it will be readily apparent to those skilled in the art that various changes in form and arrangement of parts may be made to suit requirements without departing from the spirit and scope of the invention.

We claim as our invention:

1. Apparatus to retain a corneal disc of a human cornea for altering the surface of the corneal disc by transverse planar cutting of the exposed corneal surface, said apparatus including the combination of
   a rigid support member,
   a gas-pervious molding removably carried by said rigid support member for supporting a corneal disc of a human cornea, said gas-pervious molding having a corneal disc support surface with a predetermined convex or concave curvature to shape the corneal disc for a transverse planar cut according to a required refractive power,
   means forming an evacuation chamber for communication with said gas-pervious molding,
   a pressure ring engaging said molding for releasably clamping an edge of said corneal disc between the pressure ring and said gas-pervious molding,
   a guideway means carried by said rigid support member positioned remote to said corneal disc support surface for relative movement of a cutter transversely of said corneal disc while held on said corneal disc-support surface, and
   means for adjusting the height of said guideway means relative to said corneal disc support surface.

2. The apparatus according to claim 1 wherein the circular disc receiving surface of said gas-pervious molding is concave.

3. The apparatus according to claim 1 wherein the circular disc-receiving surface of said gas-pervious molding is convex.

4. The apparatus according to claim 1 wherein said means forming an evacuation chamber is disposed to communicate with underside of said gas-pervious molding.

5. The apparatus according to claim 1 wherein said gas-pervious molding includes a plurality of openings forming said gas-pervious passageways distributed across a bottom surface thereof.

6. The apparatus according to claim 1 wherein said gas-pervious molding comprises porous material.

7. The apparatus according to claim 1 wherein said guideway means includes a cover having a threaded surface, and wherein said rigid support member includes a threaded surface to engage with the threaded surface of said cover concentrically around said gas-pervious molding.

8. The apparatus according to claim 1 wherein said pressure ring includes lugs having openings therein to receive a fastener at opposite sides of said pressure ring.

9. The apparatus according to claim 1 wherein said gas-pervious molding includes a retaining flange on the bottom end thereof to engage in a bore of said rigid support member.

10. The apparatus according to claim 1 wherein said gas-pervious molding comprises plastic material.

11. A method of altering the refractive power of a corneal disc removed from, and to replaced in, a human patient without freezing the corneal disc for such alteration, comprising the steps of supporting said corneal disc in an unfrozen condition upon the surface of a rigid gas-pervious molding having a predetermined radius of curvature to shape the corneal disc for a transverse planar cut according to a required refractive power, clamping the edge of the corneal disc against said molding, evacuating air from said gas-pervious molding to immobilize said corneal disc upon said molding, and thereafter cutting the exposed surface of said corneal disc along a plane to achieve a precalculated alteration of the refractive power of said corneal disc.

12. The method of claim 11 in which the plane of said cutting step is established by a planar guideway for a movable cutter, and in which there is the step of precisely adjusting the height of said guideway in relation to the surface of said molding prior to said supporting, clamping and cutting steps.

13. The method of claim 12 in which said cutting step comprises moving said cutter in a straight path along the plane established by said guideway.

14. The method of claim 12 in which said guideway is provided by a ring cover extending concentrically about said molding and threadedly carried by a retaining member fixed in relation to said molding; said step of adjusting the height of said guideway comprising rotating said threaded ring cover a predetermined angular distance in relation to said retaining member.

15. The method of claim 11 in which the step of clamping the edge of said corneal disc comprises bending the periphery of said disc downwardly about the edge of said molding by a clamping ring extending about said molding below said exposed surface of said corneal disc.

16. Apparatus for altering the refractive power of a corneal button comprising means for distorting a corneal button, said means including a preformed die constructed and arranged to distort a corneal button held firmly in contact with the surface of said die, and a ring located on the side of said corneal button opposite said die and constructed and arranged to press a circumferential portion of said corneal button against said die to firmly retain said portion in firm contact therewith, cutting means and reciprocating means moving one of said cutting means and said die with its associate ring transversely of each other and in spaced relation to perform a transverse planar cut on a corneal button held on said die by said ring.

17. Apparatus for altering the refractive power of a corneal button comprising means for distorting a corneal button, said means including a preformed die constructed and arranged to distort a corneal button held firmly in contact with the surface of said die, a vacuum source, said die being in contact with said source and having pores communicating with said surface and said vacuum source, and a ring constructed and arranged to press a circumferential portion of said corneal button against said die to retain and gently distort said portion in firm contact therewith, cutting means and reciprocating means moving one of said cutting means and said die with its associate vacuum source and ring transverse each other and in spaced relation to perform a transverse planar cut through a corneal button held and molded to said die by said vacuum source and said ring.

18. Apparatus as set forth in claim 17, wherein said cutting means comprises a reciprocating knife.

19. The method of modifying the refractive power of a corneal button in a manner obviating the need for a cryogenic step comprising gently supporting and distorting the shape of the button by pressing said button against a curved surface by simultaneously applying suction to the surface of the button in contact with the curved surface and applying substantially uniform mechanical pressure to the peripheral area not in contact with said surface and then while said button is retained and gently distorted by said suction and said mechanical pressure against the curved surface severing in a plane substantially transverse to the axis of said button whereby thermal and mechanical trauma are substantially reduced.

20. The method of modifying the refractive power of a corneal button in a manner obviating the need for a cryogenic step comprising gently supporting and distorting the shape of the button by pressing said button against a curved surface by simultaneously applying suction to the surface of the button in contact with the curved surface and substantially uniform mechanical pressure throughout the entire area not in contact with said surface including the edges of said button and then while said button is retained and gently distorted by said suction and said mechanical pressure against the curved surface severing in a planae substantially transverse to the axis of said button whereby thermal and mechanical trauma are substantially reduced.

21. Apparatus to retain a corneal disc of a human cornea for altering the surface of the corneal disc by transverse planar cutting of the exposed corneal surface, said apparatus including the combination of
 a rigid support member,
 a molding carried by said rigid support member for supporting a corneal disc, said molding having a corneal support surface defining a predetermined convex or concave curvature to shape the corneal disc for a transverse planar cut according to a required refractive power,
 means for releasably holding said corneal disc on said molding, and
 a guideway means carried by said rigid support member positioned remote to said disc receiving surface for relative movement of a cutter transversely of said corneal disc while held on said molding.

22. A method of altering the refractive power of a corneal disc removed from, and to be replaced in, a human patient comprising the steps of supporting a corneal disc upon the surface of a molding having a predetermined radius of curvature to shape the corneal disc for a transverse planar cut according to a required refractive power, clamping the edge of the corneal disc against said molding, and thereafter cutting the exposed surface of said corneal disc along the transverse plane to achieve a precalculated alteration of the refractive power of said disc.

* * * * *